(12) United States Patent
Feicht et al.

(10) Patent No.: US 11,473,043 B2
(45) Date of Patent: Oct. 18, 2022

(54) PHOTO-BIOREACTOR AND FILTER UNIT INTEGRATION FOR SEPARATION OF ALGAE BIOMASS

(71) Applicant: ExxonMobil Technology and Engineering Company, Annandale, NJ (US)

(72) Inventors: Sarah E. Feicht, Raritan, NJ (US); Mark A. Deimund, Jersey City, NJ (US); Everett J. O'Neal, Asbury, NJ (US); Patrick L. Hanks, Bridgewater, NJ (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 293 days.

(21) Appl. No.: 16/870,918

(22) Filed: May 9, 2020

(65) Prior Publication Data

US 2021/0024860 A1    Jan. 28, 2021

Related U.S. Application Data

(60) Provisional application No. 62/877,969, filed on Jul. 24, 2019.

(51) Int. Cl.
| | | |
|---|---|---|
| C12M 1/00 | (2006.01) | |
| B01D 61/14 | (2006.01) | |
| B01D 61/18 | (2006.01) | |
| B01D 63/02 | (2006.01) | |
| C12M 1/12 | (2006.01) | |
| C12N 1/12 | (2006.01) | |
| C10L 1/00 | (2006.01) | |

(52) U.S. Cl.
CPC ........... *C12M 21/02* (2013.01); *B01D 61/145* (2013.01); *B01D 61/18* (2013.01); *B01D 63/02* (2013.01); *C10L 1/00* (2013.01); *C12M 25/02* (2013.01); *C12M 29/14* (2013.01); *C12N 1/12* (2013.01); *B01D 2311/2688* (2013.01); *C10L 2200/0469* (2013.01); *C10L 2290/46* (2013.01); *C10L 2290/547* (2013.01)

(58) Field of Classification Search
CPC ........ C09K 13/04; C09K 13/06; C09K 13/08; H01L 21/30604; H01L 21/31111; B01D 2311/04; B01D 2311/2688; B01D 2315/06; B01D 2315/08; B01D 61/145; B01D 61/18; B01D 63/02; C10L 1/00; C10L 1/02; C10L 2200/0469; C10L 2290/46; C10L 2290/547; C12M 21/02; C12M 25/02; C12M 29/04; C12M 29/14; C12M 47/02; C12N 1/12
See application file for complete search history.

(56) References Cited

U.S. PATENT DOCUMENTS

2011/0159581 A1* 6/2011 Zhang .................... C12M 23/34
435/292.1
2013/0337518 A1* 12/2013 Razavi-Shirazi ...... C12N 11/10
435/141

* cited by examiner

*Primary Examiner* — Ellen M McAvoy
*Assistant Examiner* — Chantel L Graham
(74) *Attorney, Agent, or Firm* — Kristina Okafor (57) ABSTRACT

A system for growing and harvesting algae biomass includes a photo-bioreactor suitable for algae growth in water and a filter unit in fluid communication with the photo-bioreactor. An algae slurry, when at least partially contained within the photo-bioreactor, generates hydrostatic fluid pressure that exclusively drives the algae slurry to the filter unit and discharges a permeate.

18 Claims, 3 Drawing Sheets

PHOTO-BIOREACTOR AND FILTER UNIT INTEGRATION FOR SEPARATION OF ALGAE BIOMASS

CROSS-REFERENCE TO RELATED APPLICATIONS

This application claims priority to U.S. Provisional Application No. 62/877,969 filed Jul. 24, 2019, which is herein incorporated by reference in its entirety.

BACKGROUND OF THE INVENTION

Algaculture involves the growth and production of renewable raw materials for biofuels. The oil from harvested algae can be used directly (straight oil that is esterized into biodiesel) or refined into various biofuels, including renewable diesel and jet fuel, in addition to other chemical ingredients for products, such as cosmetics. As used herein, the term "biofuel" will refer to any type of fuel produced from algae. The carbohydrates (sugars) from algae can be fermented to make additional biofuels, including ethanol and butanol, as well as other products such as plastics and biochemicals. Biomass from algae can be used for pyrolysis oil or combined heat and power generation. Algae-derived renewable diesels and jet fuels are drop-in fuels that directly replace petroleum fuels without modification of engines. They meet all the specifications for the petroleum fuel they replace. The high lipid content, high growth rate and ability to rapidly improve strains and produce co-products, without competing for arable land, make algae an exciting addition to a sustainable fuel portfolio.

Algaculture generally involves growing algae biomass in a water slurry contained in a photo-bioreactor using photosynthetic algae strains. Reactor types include open ponds and closed reactors. During photosynthesis, green algae harvest solar energy and carbon dioxide to split water atoms, produce biomass feedstock, and release oxygen. The benefits of growing and harvesting algae includes utilization of carbon dioxide, production of oxygen, and production of oils and carbohydrates for biofuel production.

Harvesting algae from a photo-bioreactor involves separating the algae from the water in which it grows in relatively low concentrations. Algae separation processes typically involve pumping or transporting the algae and significant quantities of water to a separation device or system, which has an economic impact on the process.

SUMMARY OF THE INVENTION

The present disclosure is related to methods and apparatus for harvesting algae that is produced in bioreactors. The algae may be used for producing biofuel or other products.

In some embodiments, a system includes a photo-bioreactor suitable for algae growth in water, and a filter unit in fluid communication with the photo-bioreactor. The system may be configured such that an algae slurry, when at least partially contained within the photo-bioreactor, generates hydrostatic fluid pressure. The hydrostatic fluid pressure generated by the algae slurry may exclusively drive the algae slurry to the filter unit and discharge a permeate.

In some embodiments, a method is disclosed and includes growing algae in an algae slurry contained within a photo-bioreactor, generating hydrostatic fluid pressure with the algae slurry, and driving the algae slurry to a filter unit exclusively using the hydrostatic fluid pressure. The method may further include discharging a permeate from the filter unit.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

This disclosure relates to methods and apparatus for harvesting algae that is produced in bioreactors. The algae may be used for producing biofuel or other products.

Photosynthetic algae strains may be grown in a water slurry contained in photo-bioreactors. Types of photo-bioreactors include open ponds, open vessels, and closed vessels, and open and closed reactor vessels can exhibit a range of orientations and geometries including, but not limited to, horizontal, vertical, angled, graded tubular reactors and hanging bag reactors. Photo-bioreactors can be used to grow algae biomass from low concentrations as a seed stock for larger scale production, or be used to produce algae at a higher concentration as the primary reactor.

Harvesting algae from a photo-bioreactor involves separating the algae from the water in which it grows in relatively low concentrations. The separated water, having some residual algae and nutrients, may be recycled to the reactor to reduce the demand for new feed material. Some of the separated water, however, may be discharged for disposal or waste water treatment. Conventional systems use pumps or other means of transportation to move water from the photo-bioreactor to a separation unit and when recycling water from the separation unit back to the photo-bioreactor. In some systems, this involves transporting large quantities of water long distances, which has an adverse economic impact on the harvesting process.

The current disclosure presents systems and processes for reducing the distance that the water must be pumped, and thereby reducing the amount of energy required for operation. For at least some disclosed embodiments, the distance that the water would otherwise be pumped from a photo-bioreactor to a separation unit or the distance that the water is pumped from a separation unit back to the photo-bioreactor for recycling is reduced sufficiently to eliminate one or more pumps that would commonly be used in a conventional system. The anticipated result is a reduction in operating expenses, reduction in environmental impact, and a reduction in capital expenses for the algal grow process and, ultimately, for the algal biofuel production.

Various embodiments of the systems and processes disclosed herein include a photo-bioreactor and filter unit that may be co-located at a single or common operation site (location) for on-site filtration or separation of the algae biomass. Driven only by hydrostatic fluid pressure, an algae slurry is delivered from the photo-bioreactor to the filter unit and separated into a permeate containing most of the water and a retentate containing most of the algae that enters the filter unit. The permeate may include water, nutrients, ash, and low concentrations of algae, and the retentate may comprise a concentrated algae biomass. The permeate may be recycled to the photo-bioreactor and the concentrated algae biomass may be delivered for downstream processing. In some embodiments, the photo-bioreactor may be installed on a graded support or land, or in a vertical configuration to generate hydrostatic pressure at the filter unit to help drive the filtration operation. The filter unit may include, for example, a membrane element appropriate for filtration of algae.

Figure 1:
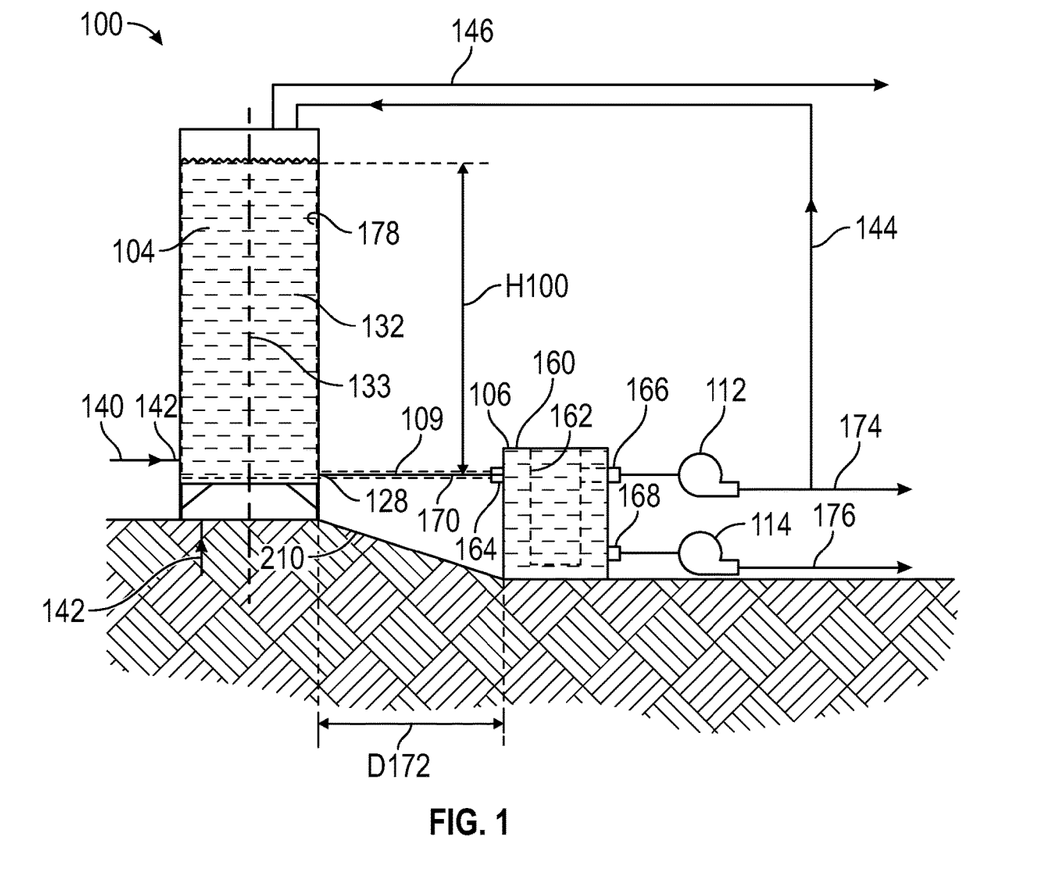
FIG. 1 is a diagram of a system capable of performing various operations for growing and harvesting algae from an algae slurry according to various embodiments of the present disclosure.

FIG. 1 is a schematic diagram of an example system 100 for growing and harvesting algae biomass, according to various embodiments. System 100 includes a photo-bioreactor 104 suitable for growing algae in water and a separation unit, which in this example is a filter unit 106, in fluid communication with photo-bioreactor 104 through a discharge line 109. System 100 can also include a permeate pump 112 and a retentate pump 114, both downstream from and in fluid communication with output ports of filter unit 106.

Photo-bioreactor 104, alternately referred to herein as "reactor 104," includes a feed inlet 122 and a slurry outlet 128, each in fluid communication with a reactor volume that extends within reactor 104 along a longitudinal axis 133. Reactor 104 may contain fluids and algae to facilitate algae growth within the reactor volume. In FIG. 1, photo-bioreactor 104 is a closed, vertical vessel with a generally vertical-oriented longitudinal axis 133. In other embodiments, however, the longitudinal axis 133 may be horizontal, or may be diagonally oriented between vertical and horizontal. Thus, in various embodiments, longitudinal axis 133 is not horizontal.

Reactor 104 includes a fluid level 134 suitable for operation of system 100. Fluid level 134 may be a pre-established location for maintaining a targeted volume of fluid in reactor 104 or may be an operation parameter that reflects a current, variable volume of fluid. For example, fluid level 134 may be monitored or maintained using a sensor or flow valve that can detect fluid or the top surface of fluid, such as an algae slurry. Fluid level 134 may be at or below the maximum capacity of reactor 104. Fluid level 134 may be located at, above, or below feed inlet 122. In some examples, fluid level 134 is selected or adjusted to accommodate operational needs. In some examples, fluid level 134 may change due to various occurrences, for example by evaporation, with or without compensation during a period of operation.

A feed line 140 is fluidically coupled to reactor 104 at feed inlet 122 to provide a feed stream when needed. The feed stream may include water, nutrients, and algae starter materials, as examples, in variable concentrations as may be needed. In some operations, the feed stream may include water and nutrients without algae starter materials, relying on existing algae in reactor 104 or algae recycled to reactor 104 after leaving reactor 104.

A sparge line 142 may also be fluidically coupled to reactor 104 to provide a sparge stream of one or more gases, such as carbon dioxide, air, and possibly other nutrients to be injected into the fluid held in reactor 104. The carbon dioxide may come from any suitable source, including atmospheric air, an exhaust stream from a combustion process, or a storage location including tanks or geological formations, as examples. As with others of the lines coupled to reactor 104, sparge line 142 may represent a plurality of sparge lines fluidically coupled to reactor 104 at one or more locations. Also for the purpose of delivering and distributing the sparge stream, sparge line 142 may be coupled to one or more nozzles within reactor 104.

Filter unit 106 may be any type of filter or separator capable of separating algae from water. As illustrated, filter unit 106 includes a filter body 160, a filter element 162 coupled to, held within, or forming part of body 160, a filter inlet 164, a permeate outlet 166 to discharge a permeate, and a retentate outlet 168 to discharge a retentate. In some embodiments, filter unit 106 may comprise an ultrafiltration membrane unit, such as a hollow fiber membrane unit or a size exclusion membrane unit, and filter element 162 would be selected correspondingly.

Discharge line 109 fluidically couples slurry outlet 128 of reactor 104 to filter inlet 164. Thus, discharge line 109, slurry outlet 128, and filter inlet 164 define a fluid coupling 170 that operatively couples filter unit 106 to photo-bioreactor 104. Slurry outlet 128 or filter inlet 164 may include a fitting or may simply be an aperture through the wall of reactor 104 or filter body 160, as examples.

Filter outlets 166, 168 may be located at a same elevation on filter body 160 or may be located at different elevations on filter unit 106. Permeate outlet 166 may be located at an elevation below the elevation of fluid level 134 to drive fluid flow through filter element 162 and permeate outlet 166. The suction end of permeate pump 112 is in fluid communication with permeate outlet 166.

A recycling line or path 144 is fluidically coupled between filter unit 106 and reactor 104 for returning fluids from other parts of system 100 to reactor 104. An off-gas line 146 is fluidically coupled to reactor 104 to discharge a product or by-product gas or excess sparge gas from reactor 104. Gas discharged through off-gas line 146 may be sent for storage or emitted to the atmosphere, as examples. Together or alone, the product gas or excess sparge gas may be referenced as a discharge gas. The product gas may be a mixture including oxygen produced by the algae. In some embodiments, permeate pump 112 may be used to help convey the permeate to the reactor 104 via the recycling path 144. In other embodiments, or in addition thereto, the permeate pump 112 may also be in fluid communication with a disposal line 174 that conveys a portion of the permeate to waste water treatment. One or more valves (not shown) may be included to regulate the distribution of flow from permeate pump 112 to reactor 104 via the recycling path 144 or through disposal line 174. In the example shown, recycling path 144 is a direct connection between filter unit 106 and bioreactor 104, having no storage location, such as a tank, pond, or a tank trailer, fluidically coupled between filter unit 106 and bioreactor 104.

The suction of retentate pump 114 may be in fluid communication with retentate outlet 168 of filter unit 106 to help move retentate from outlet 168. The discharge of retentate pump 114 is in fluid communication with a product line 176 for algae processing. During operation, filter element 162 collects retentate containing a majority of the algae that enters the filter unit 106 from discharge line 109. Retentate may be removed or harvested from filter unit 106 by a manual or an automated process. In at least some embodiments, filter unit 106 includes an arrangement or mechanism that allows the algae biomass retentate to be removed and discharged through retentate outlet 168 without an operator accessing filter element 162. The harvested retentate may be processed into biofuel.

System 100 includes an operational volume 178 that may contain an algae slurry. Operational volume 178 extends within the reactor volume of reactor 104 and may extend to filter inlet 164. The general location of operational volume 178 in FIG. 1 is shown with a dashed enclosure. In some examples, operational volume 178 extends to filter permeate outlet 166 or to a fluidically coupled location beyond permeate outlet 166. Operational volume 178 is at least partially defined in the vertical direction by a fluid height H100 that describes the vertical distance from the fluid level 134 in reactor 104 down to a datum location that is lower than fluid level 134. In the example of FIG. 1, the datum location of fluid height H100 is filter inlet 164. Filling operational volume 178 with algae slurry generates a fluid column that develops hydrostatic pressure. Operational volume 178 and, when filled, its fluid column extend from fluid level 134 of reactor 104 through fluid coupling 170 (e.g., discharge line 109) to inlet 164 of filter unit 106, which may be measured vertically by fluid height H100. In some examples, operational volume 178 may also extend through filter unit 106. In some examples, operational volume 178 may also extend through filter unit 106 and into a fluidically coupled line that is beyond filter unit 106. In such embodiments, fluid height H100 may be measured from a datum location that is beyond filter unit 106 and is, in some examples, lower than inlet 164 of filter unit 106. Discharge line 109 may include a reduction in elevation or may be horizontal as it extends toward filter unit 106, adding to fluid height H100 of operational volume 178.

Thus in FIG. 1, the algae slurry contained within operational volume 178 defines or otherwise provides a fluid column that extends to a fluid height H100 above the filter inlet 164. In some cases, the fluid height H100 can extend to the fluid level 134 as shown in FIG. 1, but that is not necessary. Operational volume 178 extends through the discharge line 109 when present. Without the aid of a pump, the fluid pressure generated by the algae slurry contained within operational volume 178 may be used to drive a permeate of the algae slurry through the filter unit 106 to separate the permeate and the retentate. Permeate may be discharged through outlet 166 as a steady stream during operation. Alternatively, permeate, driven by fluid pressure in operational volume 178, may discharge through permeate outlet 166 intermittently or as a trickle or as drips during other modes or stages of operation, as might occur, for example, if filter element 162 becomes partially clogged. Permeate pump 112 may serve to help remove fluid that has been driven through permeate outlet 166 by the hydrostatic pressure of operational volume 178. In some examples, permeate pump 112 may help to draw fluid through filter unit 106.

The fluid pressure in operational volume 178 includes the hydrostatic pressure generated by the fluid height H100 of the algae slurry that is disposed in operational volume 178. During operation, fluid pressure in operational volume 178 is greater than the pressure drop that occurs while permeate flows from reactor 104 through a permeate discharge path that includes fluid coupling 170, filter body 160, filter element 162, and permeate outlet 166. The pressure drop that may be overcome by the fluid pressure of operational volume 178 includes frictional pressure drop in the permeate discharge path.

Filter unit 106 may be disposed at a separation distance D172 from the photo-bioreactor 104. Fluid coupling 170 extends through the separation distance D172, but due to the possibility of bends (e.g., structural bends or bends within an internal fluid passage), the total path length of fluid coupling 170 may be equal or greater than the separation distance D172. The total path length of fluid coupling 170 refers to the total distance that fluid must flow to pass through coupling 170. The length of discharge line 109 is less than or equal to total path length of fluid coupling 170. Like total path length of fluid coupling 170, the length of discharge line 109 may be equal or greater than the separation distance D172 due to the possibility of bends. The length of separation distance D172 and the total path length of fluid coupling 170 are selected or limited to ensure that the pressure drop through fluid coupling 170 and filter unit 106 that occurs during operation is less than fluid pressure in operational volume 178 so permeate may flow freely without requiring the aid of a pump. Operational volume 178 extends through fluid coupling 170 and therefore through the total path length of fluid coupling 170 and through the separation distance D172.

In various embodiments, separation distance D172 is 30 meters or less, 10 meters or less, or 1 meter or less. In various embodiments, the total path length of fluid coupling 170 is 30 meters or less, 10 meters or less, or 1 meter or less. In various embodiments, slurry outlet 128 of reactor 104 is immediately adjacent filter inlet 164. In some embodiments, separation distance D172 or the total path length of fluid coupling 170 is greater than 30 meters.

Figure 2:
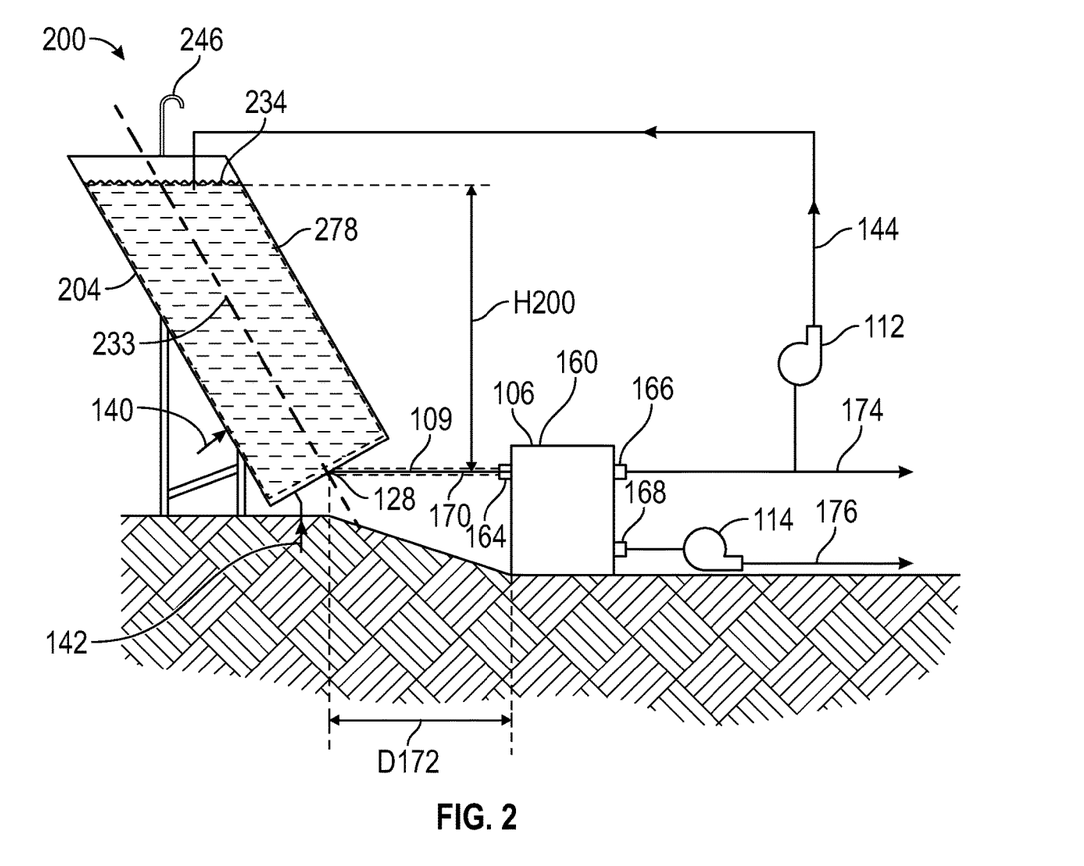
FIG. 2 is a diagram of another system capable of performing various operations for growing and harvesting algae according to various embodiments of the present disclosure.

FIG. 2 is a schematic diagram of another example system 200 for growing and harvesting algae biomass from an algae slurry, according to one or more additional embodiments. System 200 may be similar in some respects to system 100 of FIG. 1 and therefore system 200 may be best understood with reference thereto, where like numerals will represent like components that may not be described again in detail. System 200 includes a photo-bioreactor 204 suitable for growing algae in water, filter unit 106 in fluid communication with photo-bioreactor 204 through discharge line 109, permeate pump 112, and retentate pump 114. Filter unit 106 may be located proximal the photo-bioreactor 204. System 200 further includes recycling line or path 144 and disposal line 174, as described herein.

The fluidic connections or physical arrangements between and from reactor 204, filter unit 106, discharge line 109, permeate pump 112, retentate pump 114, and other similarly numbered components may be similar to the corresponding fluidic connections or physical arrangements of system 100, including the potential variations that were described above. In general, the operations, including the potential operational variations, described for system 100, also pertain to system 200. However, in this example, disposal line 174 fluidically communicates with permeate outlet 166 in parallel with permeate pump 112.

In FIG. 2, photo-bioreactor 204, alternately referred to herein as reactor 204, is a generally closed vessel that includes slurry outlet 128 and a vent 246 for off-gassing, both in fluid communication with a reactor volume, which extends along a diagonal longitudinal axis 233. Reactor 204 may contain fluids and algae to facilitate algae growth. In general, longitudinal axis 233 may be diagonal (i.e., angled between vertical and horizontal) as shown in FIG. 2, but may alternatively be vertical or horizontal, without departing from the scope of the disclosure. Reactor 204 includes a fluid level 234 suitable for operation of system 200. Fluid level 234 may operate similar to fluid level 134 (FIG. 1) and, likewise, may be monitored or maintained. Vent 246 may be open to the atmosphere to discharge a product or by-product gas or excess sparge gas from reactor 104. Some embodiments may capture the off-gas from vent 246.

System 200 includes a fluid height H200 that describes the vertical distance from the fluid level 234 of reactor 104 down to a datum location that is lower than fluid level 234. For example, filter inlet 164 or permeate outlet 166 may be located at an elevation below the elevation of fluid level 234 to allow the hydrostatic pressure of the algae slurry contained within reactor 204 to exclusively (independently) drive fluid flow through filter element 162. In the example of FIG. 2, the datum location of fluid height H200 is filter inlet 164. When at least discharge line 109 and reactor 204 are filled up to level 234 with algae slurry, system 200 includes an operational volume 278 of fluid that defines a fluid column that extends to fluid height H200, and operational volume 278 extends from fluid level 234 of reactor 204 through fluid coupling 170 to filter unit 106. Filter unit 106 may be disposed at a separation distance D172 from the photo-bioreactor 204, spanned by fluid coupling 170. During operation, fluid pressure generated by the algae slurry contained in operational volume 278 drives the algae slurry through filter unit 106 and permeate is discharged through outlet 166 without the aid of any pump.

Figure 3:
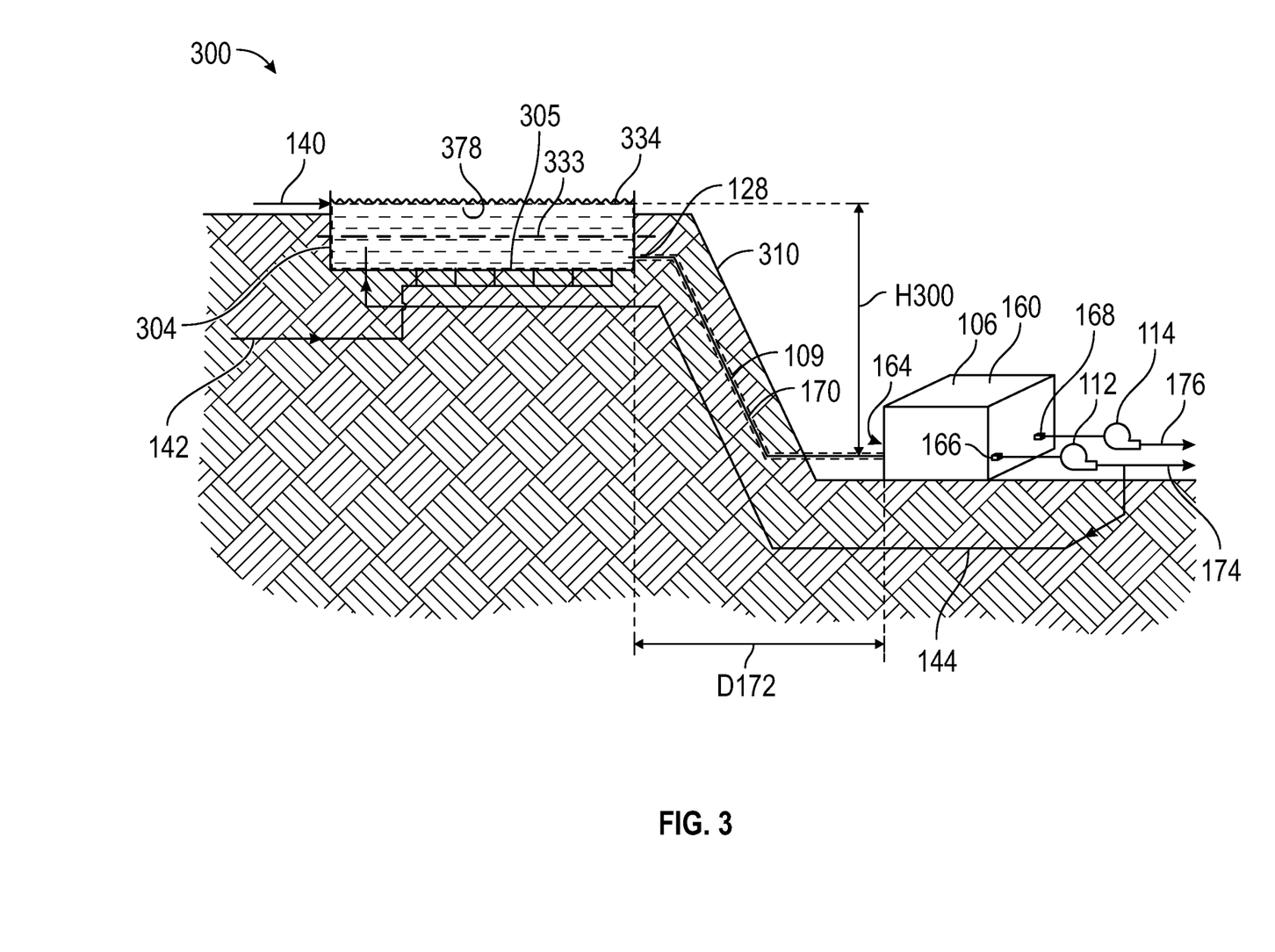
FIG. 3 is a diagram of still another system capable of performing various operations for growing and harvesting algae according to various embodiments of the present disclosure.

FIG. 3 is a schematic diagram of another example system 300 for growing and harvesting algae biomass from an algae slurry, according to various embodiments. System 300 may be similar in some respects to system 100 of FIG. 1 or system 200 of FIG. 2 and therefore may be best understood with reference thereto, where like numerals will represent like components that may not be described again in detail. System 300 includes a photo-bioreactor 304 suitable for growing algae in water, filter unit 106 in fluid communication with photo-bioreactor 304 through discharge line 109, permeate pump 112, and retentate pump 114. Filter unit 106 may be located proximal the photo-bioreactor 304. System 300 also includes recycling line or path 144 and disposal line 174. The fluidic connections or physical arrangements between and from reactor 304, filter unit 106, discharge line 109, permeate pump 112, retentate pump 114, and other similarity numbered components may be similar to the corresponding fluidic connections or physical arrangements of system 100, including the potential variations that were described. In general, the operations, including the potential operational variations, described for system 100, also pertain to system 300.

In FIG. 3, discharge line 109 includes a reduction in elevation as it extends toward filter unit 106, which helps generate additional hydrostatic pressure when discharge line 109 is filled with algae slurry, water, etc. The drop in elevation of discharge line 109 from reactor 304 to filter unit 106 may be up to 6 meters, for example. Thus, in some embodiments, discharge line 109 may be horizontal and otherwise lack a reduction in elevation. Thus, in various embodiments, drop in elevation of discharge line 109 may be selected within the range of 0-6 m. Some embodiments may have a different value for the change in elevation of discharge line 109.

In FIG. 3, photo-bioreactor 304, which will also be called reactor 304, is an open pond having a base 305. In the illustrated embodiment, the base 305 slopes downward parallel to a longitudinal axis 133 of the reactor 304 and toward filter unit 106, but in other embodiments, the base 304 and the longitudinal axis 133 may be horizontal and otherwise not slope toward the filter unit 106, without departing from the scope of the disclosure. Photo-bioreactor 304 includes slurry outlet 128 in fluid communication with a reactor volume extending within reactor 304 along a diagonal longitudinal axis 333. Reactor 304 may contain fluids and algae to facilitate algae growth, and includes a fluid level 334 suitable for operation of system 300. Fluid level 334 and may vary as described of fluid level 134 (FIG. 1) and, likewise, may be monitored or maintained.

System 300 includes a fluid height H300 that describes the vertical distance from the fluid level 334 of reactor 104 down to a datum location that is lower than fluid level 334. For example, filter inlet 164 or permeate outlet 166 may be located at an elevation below the elevation of fluid level 334 to drive fluid flow through filter element 162 and permeate outlet 166. Fluid height H300 includes the drop in elevation of discharge line 109, which is described above. In the example of FIG. 3, the datum location of fluid height H300 is filter inlet 164. When at least discharge line 109 and reactor 304 are filled up to level 334 with algae slurry, system 300 includes an operational volume 278 of fluid that defines a fluid column that extends through fluid height H300. Operational volume 378 extends from fluid level 334 of reactor 304 through fluid coupling 170 to filter unit 106. Filter unit 106 is disposed at a separation distance D172 from the photo-bioreactor 304, spanned by fluid coupling 170. During operation, hydrostatic fluid pressure generated by the algae slurry contained within operational volume 378 independently drives the algae slurry through filter unit 106 and permeate is discharged through outlet 166 without the aid of any pump.

In any of systems 100, 200, 300 of FIGS. 1, 2, and 3, respectively, no pump is required to pump the algae slurry between photo-bioreactor 104, 204, 304 and filter unit 106, which reduce capital costs and operational costs for the system, as compared to conventional systems. Rather, the flow of the algae slurry to and through filter unit 106 is driven entirely and exclusively by the hydrostatic pressure of the algae slurry contained within operational volumes 178, 278, 378. In at least one embodiment, however, a pump may be fluidically coupled between a photo-bioreactor 104, 204, 304 and filter unit 106, and the pump may be called a pre-filter pump. The pre-filter pump may provide pressure to increase the flow rate of fluid through recycling line 144, disposal line 178, or product line 176. The pre-filter pump may provide a portion the pressure required to drive fluid through a filter unit 106. Some embodiments of system 100, 200, 300 may be configured without a permeate pump 112, a retentate pump 114, or a recycling line 144.

In various examples of systems 100, 200, 300 of FIGS. 1, 2, and 3, respectively, the datum location for fluid height H100, H200, H300 of operational volume 178, 278, 378, respectively, is permeate outlet 166 of filter unit 106. Then, the fluid column or operational volume may be evaluated as extending from fluid level 134, through fluid coupling 170, through filter unit 106, and to permeate outlet 166. In various examples of system 100, 200, 300, the datum location for fluid height is selected to be a location that is fluidically coupled to permeate outlet 166 and is lower than fluid level 134. As an example, a selected datum location may be in a line that extends beyond permeate outlet 166. Therefore, selected datum location may be disposed prior to permeate pump 112, at the suction of permeate pump 112, after permeate pump 112, along recycling line 144, or along disposal line 174. Some examples the fluidic path that includes the selected datum location and extends beyond permeate outlet 166 is free of any pump, as shown in FIG. 2, but this alterative may also be applied to some embodiments of FIGS. 1 and 3. The operational volume 178, 278, 378, respectively, may be evaluated as extending from fluid level 134, 234, 334 down to that selected datum location.

This placement of the datum location may be used, for example, if the suction of permeate pump 112 or the selected location along recycling line 144 or the selected location along disposal line 174 is lower than filter inlet 164 or permeate outlet 166. This evaluation may be use, for example, if filter inlet 164 or permeate outlet 166 is above slurry outlet 128 on the reactor or is near, at, or above a fluid level 134, 234, 334. The selected datum location that is fluidically coupled beyond filter unit 106 is at a distance below the fluid level 134, 234, 334 that generates a pressure head sufficient to drive or pull fluid flow through filter element 162 and permeate outlet 166. In some embodiments, an operational volume described herein generates a pressure head sufficient to drive or pull fluid flow through filter element 162 and permeate outlet 166 and through a line fluidically coupled beyond permeate outlet 166, a line such as disposal line 174, without the operation of a permeate pump 112. Establishing the datum location for fluid height as described here may provide a better or more complete evaluation of the fluid pressure that may be available to cause fluid to pass through a filter unit 106 without requiring the aid of a pump in various examples.

In addition to the examples disclosed above, other embodiments based those examples may include a photo-bioreactor that is a horizontal tubular reactor, vertical tubular reactor, a vertical vessel, a horizontal vessel, a hanging bag reactor, or a pond as examples. Although, some photo-bioreactors described herein have included a longitudinal axis, some embodiments include a photo-bioreactor with a shape that may not include a longitudinal axis, a shape such as spherical, cubic, conical with base equal to height, or irregular, as examples. Embodiments may include multiple reactors or multiple filtration units configured to operate in parallel or in series. Photo-bioreactor reactors for the disclosed embodiments may be closed or open to the atmosphere.

During some example operations of system 100, discharge line 109 contains from 0 to 5 wt % algae and from 95 to 100 wt % water and nutrients, recycling path 144 or disposal line 174 contains from 0 to 1 wt % algae and from 99 to 100 wt % water, and the retentate in line 176 includes 1 to 15 wt % algae and from 85 to 99 wt % water. Systems 200, 300 may operate with similar concentrations.

Listing of Exemplary Embodiments

Clause 1. A system that includes a photo-bioreactor suitable for algae growth in water; and a filter unit in fluid communication with the photo-bioreactor, wherein the system is configured such that an algae slurry, when at least partially contained within the photo-bioreactor, generates hydrostatic fluid pressure wherein the hydrostatic fluid pressure generated by the algae slurry exclusively drives the algae slurry to the filter unit and discharges a permeate.

Clause 2. The system of clause 1, wherein the photo-bioreactor is selected from the group consisting of a pond, a closed vessel, an open vessel, a horizontal tubular reactor, a vertical tubular reactor, a graded tubular reactor, a spherical vessel, and a hanging bag.

Clause 3. The system of clause 1 or 2, wherein the filter unit comprises an ultrafiltration membrane unit.

Clause 4. The system of clause 3, wherein the ultrafiltration membrane unit comprises one of a hollow fiber membrane unit and a size exclusion membrane unit.

Clause 5. The system of any clause 1 to 4, wherein the filter unit is disposed at a separation distance from the photo-bioreactor and the separation distance includes a reduction in elevation between the photo-bioreactor and an inlet to the filter unit.

Clause 6. The system of any clause 1 to 5, wherein the photo-bioreactor exhibits a non-horizontal longitudinal axis.

Clause 7. The system of any clause 1 to 6, further comprising a recycling path extending from a permeate outlet of the filter unit to the photo-bioreactor to return a portion of the permeate to the photo-bioreactor.

Clause 8. The system of clause 7, further comprising a pump disposed between the permeate outlet and the photo-bioreactor, wherein the pump is operable to return the portion of permeate to the photo-bioreactor.

Clause 9. The system of clause 7 or 8, wherein the portion is a first portion of the permeate and the system further includes a disposal line extending from the permeate outlet to receive a second portion of the permeate for disposal.

Clause 10. The system of any clause 1 to 9, further comprising an operational volume extending within the photo-bioreactor and to a fluidly coupled datum location selected from a group including an inlet of the filter unit, a permeate outlet of the filter unit, and a location in a line that extends beyond the permeate outlet, herein without the aid of a pump, the hydrostatic fluid pressure generated by the algae slurry contained within operational volume drives the permeate through the filter unit.

Clause 11. A method that includes growing algae in an algae slurry contained within a photo-bioreactor; generating hydrostatic fluid pressure with the algae slurry; driving the algae slurry to a filter unit exclusively using the hydrostatic fluid pressure; and discharging a permeate from the filter unit.

Clause 12. The method of clause 11, further comprising pumping a portion of the permeate to the photo-bioreactor with a pump fluidically disposed between a permeate outlet and the photo-bioreactor.

Clause 13. The method of clause 12, wherein the portion is a first portion of the permeate and the method further comprises conveying a second portion of the permeate to be treated as waste water.

Clause 14. The method of any clause 11 to 13, further comprising harvesting a retentate from the filter unit.

Clause 15. The method of clause 14, wherein the retentate comprises 1 to 15 wt % algae and 85 to 99 wt % water.

Clause 16. The method of clause 14 or 15, further comprising processing the retentate into biofuel.

Clause 17. The method of any clause 11 to 16, wherein the filter unit is disposed at a separation distance from the photo-bioreactor, and the method also includes flowing the algae slurry along the separation distance; and changing elevation between the photo-bioreactor and an inlet to the filter unit as the algae slurry flows along the separation distance.

Clause 18. The method of any clause 11 to 17, wherein the filter unit comprises an ultrafiltration membrane unit selected from the group consisting of a hollow fiber membrane unit and a size exclusion membrane unit.

Clause 19. The method of any clause 11 to 18, wherein the photo-bioreactor is selected from the group consisting of a pond, a closed vessel, an open vessel, a horizontal tubular reactors, a vertical tubular reactors, a graded tubular reactor, a spherical vessel, and a hanging bag.

Clause 20. The method of any clause 11 to 19, wherein an operational volume extends from the photo-bioreactor to a fluidly coupled datum location located beyond an inlet of the filter unit, the datum location being selected from the group consisting of a permeate outlet of the filter unit and a location in a line that extends beyond the permeate outlet, wherein without the aid of a pump, the hydrostatic fluid pressure generated by the algae slurry contained within operational volume drives the permeate through the filter unit to separate the permeate and the retentate.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The illustrative embodiments disclosed herein suitably may be implemented in the absence of any element that is not specifically disclosed herein and/or any optional element disclosed herein.

Nomenclature

While compositions and methods are described in terms of "comprising," "containing," or "including" various components or steps, the compositions and methods can also "consist essentially of" or "consist of" the various components and steps. For the methods herein, the order of various process steps may be rearranged in some embodiments and yet remain within the scope of the disclosure, including the claims.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a to b") disclosed herein is to be understood to set forth every number and range encompassed within the broader range of values. Also, the terms used herein, including the claims, have their plain, ordinary meaning unless otherwise explicitly and clearly defined by the patentee. Moreover, the indefinite articles "a" or "an," as used herein, including the claims, are defined herein to mean one or more than one of the element that it introduces.

The term "or" as used in a phrase such as "A or B" herein is intended to include optionally of any of the following: "A" alone, "B" alone, and, where feasible, "A and B." Ordinal numbers such as first, second, third, etc. do not indicate a quantity but are used for naming and reference purposes. In addition, ordinal numbers used in the claims in reference to a component or feature may differ from the ordinal numbers used in the written description for the corresponding component or feature. For example, a "second object" in a claim might be described as a "third object" or may be described without an ordinal number in the written description.

As used herein, including the claims, the term "line" for fluid communication may include any of the following pipe, piping, tubing, hose, fittings, valves, gauges, check valves, flow meters, filters, and the like.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

For the sake of clarity, not all features of a physical embodiment are described or shown in this application. It is understood that in the development of a physical embodiment incorporating the embodiments of the present disclosure, numerous implementation-specific decisions must be made to achieve the developer's goals, such as compliance with system-related, business-related, government-related, and other constraints, which vary by implementation and from time to time. While a developer's efforts might be time-consuming, such efforts would be, nevertheless, a routine undertaking for those of ordinary skill in the art and having benefit of this disclosure.

What is claimed is:

1. A system comprising:
   a photo-bioreactor suitable for algae growth in water; and
   a filter unit in fluid communication with the photo-bioreactor, the filter unit disposed at a separation distance from the photo-bioreactor and the separation distance includes a reduction in elevation between the photo-bioreactor and an inlet to the filter unit,
   wherein the system is configured such that an algae slurry, when at least partially contained within the photo-bioreactor, generates hydrostatic fluid pressure;
   wherein the hydrostatic fluid pressure generated by the algae slurry exclusively drives the algae slurry to the filter unit and discharges a permeate.

2. The system of claim 1, wherein the photo-bioreactor is selected from the group consisting of a pond, a closed vessel, an open vessel, a horizontal tubular reactor, a vertical tubular reactor, a graded tubular reactor, a spherical vessel, and a hanging bag.

3. The system of claim 1, wherein the filter unit comprises an ultrafiltration membrane unit.

4. The system of claim 3, wherein the ultrafiltration membrane unit comprises one of a hollow fiber membrane unit and a size exclusion membrane unit.

5. The system of claim 1, wherein the photo-bioreactor exhibits a non-horizontal longitudinal axis.

6. The system of claim 1, further comprising a recycling path extending from a permeate outlet of the filter unit to the photo-bioreactor to return a portion of the permeate to the photo-bioreactor.

7. The system of claim 6, further comprising a pump disposed between the permeate outlet and the photo-bioreactor, wherein the pump is operable to return the portion of permeate to the photo-bioreactor.

8. The system of claim 6, wherein the portion is a first portion of the permeate and the system further includes a disposal line extending from the permeate outlet to receive a second portion of the permeate for disposal.

9. The system of claim 1, further comprising an operational volume extending within the photo-bioreactor and to a fluidly coupled datum location selected from a group including an inlet of the filter unit, a permeate outlet of the filter unit, and a location in a line that extends beyond the permeate outlet,
   wherein without the aid of a pump, the hydrostatic fluid pressure generated by the algae slurry contained within operational volume drives the permeate through the filter unit.

10. A method comprising:
growing algae in an algae slurry contained within a photo-bioreactor;
generating hydrostatic fluid pressure with the algae slurry;
driving the algae slurry to a filter unit exclusively using the hydrostatic fluid pressure; and
discharging a permeate from the filter unit,
wherein the filter unit disposed at a separation distance from the photo-bioreactor and the separation distance includes a reduction in elevation between the photo-bioreactor and an inlet to the filter unit.

11. The method of claim 10, further comprising pumping a portion of the permeate to the photo-bioreactor with a pump fluidically disposed between a permeate outlet and the photo-bioreactor.

12. The method of claim 11, wherein the portion is a first portion of the permeate and the method further comprises conveying a second portion of the permeate to be treated as waste water.

13. The method of claim 10, further comprising harvesting a retentate from the filter unit.

14. The method of claim 13, wherein the retentate comprises 1 to 15 wt % algae and 85 to 99 wt % water.

15. The method of claim 13, further comprising processing the retentate into biofuel.

16. The method of claim 10, wherein the filter unit comprises an ultrafiltration membrane unit selected from the group consisting of a hollow fiber membrane unit and a size exclusion membrane unit.

17. The method of claim 10, wherein the photo-bioreactor is selected from the group consisting of a pond, a closed vessel, an open vessel, a horizontal tubular reactors, a vertical tubular reactors, a graded tubular reactor, a spherical vessel, and a hanging bag.

18. The method of claim 10, wherein an operational volume extends from the photo-bioreactor to a fluidly coupled datum location located beyond an inlet of the filter unit, the datum location being selected from the group consisting of a permeate outlet of the filter unit and a location in a line that extends beyond the permeate outlet,
wherein without the aid of a pump, the hydrostatic fluid pressure generated by the algae slurry contained within operational volume drives the permeate through the filter unit to separate the permeate and the retentate.

* * * * *